(12) United States Patent
Behle

(10) Patent No.: US 7,972,059 B2
(45) Date of Patent: Jul. 5, 2011

(54) X-RAY CASSETTE COVER

(76) Inventor: Sherry Behle, St. Louis County, MO (US)

(*) Notice: Subject to any disclaimer, the term of this patent is extended or adjusted under 35 U.S.C. 154(b) by 0 days.

(21) Appl. No.: 12/476,646

(22) Filed: Jun. 2, 2009

(65) Prior Publication Data

US 2009/0316861 A1  Dec. 24, 2009

Related U.S. Application Data

(60) Provisional application No. 61/058,013, filed on Jun. 2, 2008.

(51) Int. Cl.
*G03B 42/04* (2006.01)

(52) U.S. Cl. ........ 378/177; 378/167; 378/182; 378/189; 378/190

(58) Field of Classification Search ............ 378/167, 378/177, 182, 189, 190
See application file for complete search history.

(56) References Cited

U.S. PATENT DOCUMENTS

| | | | |
|---|---|---|---|
| 3,843,041 A | 10/1974 | Oliverius | |
| 4,961,502 A | 10/1990 | Griffiths | |
| 5,178,278 A * | 1/1993 | Oliverius | 206/455 |
| 5,185,776 A | 2/1993 | Townsend | |
| 5,377,254 A * | 12/1994 | Walling | 378/167 |
| 5,519,229 A | 5/1996 | Verbeke et al. | |
| 5,773,839 A | 6/1998 | Krepel et al. | |
| 6,765,984 B2 * | 7/2004 | Higgins et al. | 378/37 |
| 6,967,333 B2 * | 11/2005 | Hata | 250/370.11 |
| 7,505,555 B2 * | 3/2009 | Hermann et al. | 378/37 |
| 7,632,013 B1 * | 12/2009 | Bueltmann | 378/204 |

* cited by examiner

*Primary Examiner* — Edward J Glick
*Assistant Examiner* — Thomas R Artman
(74) *Attorney, Agent, or Firm* — Richard L. Marsh

(57) ABSTRACT

An X-ray cover for enveloping an X-ray cassette. The cover comprises a first sheet of non-plastic material and a second sheet of non-plastic material. The cover further comprises a cushion element integrally distributed throughout the first sheet and the second sheet wherein the first sheet and second sheet are sized and shaped to accept the X-ray cassette and wherein the cushion element is sized and shaped to cushion the patient's body part during an X-ray procedure.

4 Claims, 1 Drawing Sheet

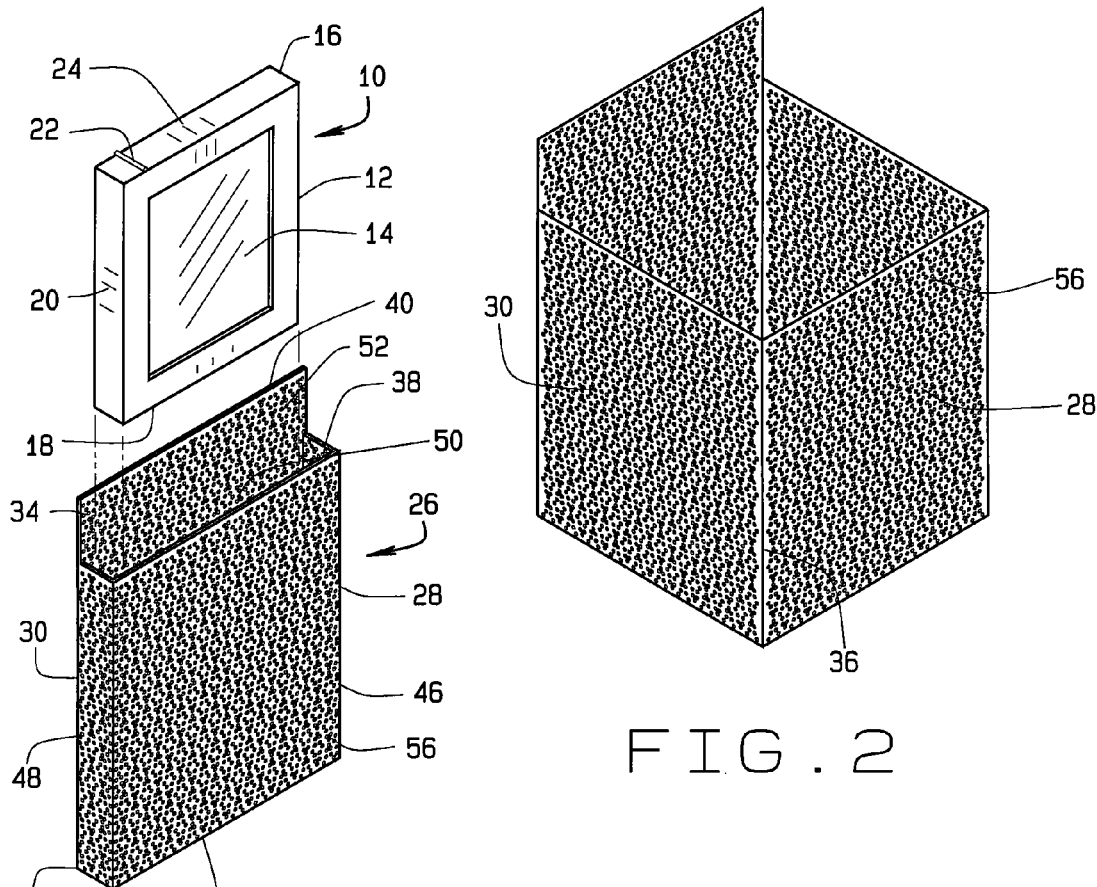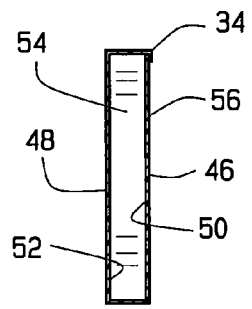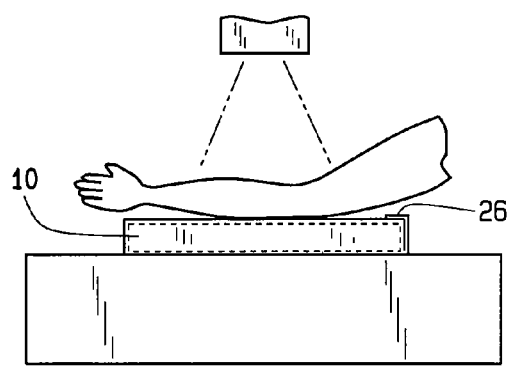

X-RAY CASSETTE COVER

CROSS-REFERENCE TO RELATED APPLICATIONS

This application claims priority under 35 U.S.C. §119(e) to U.S. Provisional Patent Application No. 61/058,013 filed Jun. 2, 2008, in the name of the present inventor and entitled "X-Ray Cassette Cover" and is incorporated herein by reference.

STATEMENT REGARDING FEDERALLY SPONSORED RESEARCH

Not Applicable.

BACKGROUND OF THE DISCLOSURE

The present invention relates to a disposable, sterile cover for enclosing a non-sterile article and a method for enclosing the non-sterile article. More specifically, the present disclosure relates to a cover for an X-ray cassette. The cover is disposable to prevent the spread of germs, aiding in infection control, cassette protection and more convenient handling of patients by healthcare professionals.

In conventional radiography (also known as "X-ray photography" or "X-ray procedure), a plate is made by forming one or more emulsion layers on a flexible film base which is supported within a light-tight, non-sterile cassette. The interior of the cassette is coated with one or more X-ray sensitive luminescent layers. In use, the non-sterile cassette must be isolated from the sterile site or field of operation.

During use, the health care professional loads the cassette containing an unexposed X-ray plate into an X-ray machine or positions the cassette in patient contact whichever is appropriate for an ordered exam. After exposure, the health care professional removes the exposed cassette and X-ray plate for development and subsequent fixing of the latent image produced.

It will be appreciated by those skilled in the art that X-ray cassettes are one of the few medical devices which are reused. It will further be appreciated by those skilled in the art that X-ray cassettes can be very impersonal and very uncomfortable to the patient. For example, X-ray cassettes used in portable radiography and tabletop radiography are cold and hard. Often times, patients must be placed on the X-ray cassette, thereby making the patient less comfortable and less cooperative.

X-ray cassettes, during their repeated use, may directly contact the patient's skin or patient's fluids leading to unsanitary conditions as germs of one patient pass onto another patient and/or the health care personnel handling the X-ray cassette. Germs such as Staph can unknowingly pass from patient to patient, therefore leading to a large contribution to the loss of life.

In some instances where X-rays are required to be taken during trauma cases, the cassette is often contaminated with the blood of a patient and these contaminants may be potential health hazards to the health care professional who must handle the X-ray cassette for development. Further, dangers from bacteria exist to personnel handling the X-ray cassette. Accordingly, protecting cassettes from contamination is highly desirable for safety reasons. Cassettes are also very expensive; and once blood and other fluids seep into the cassettes, the cassettes have to be repaired or replaced.

Health care professionals use cassette covers to enclose the cassette during the X-ray procedure. Current cassette covers, however, are made of plastic. These plastic covers, however, adhere to the patient's skin via the patient's sweat, blood or other fluids leading to uncomfortable conditions for the patient and to unwieldy handling by the health care professional. Further, existing plastic covers do not cushion the patient or absorb the patient's fluids. Health care professionals require cassette covers that aid in safety, patient comfort and ease of disposal.

SUMMARY

The present disclosure relates to a sterile cover configured to seal an X-ray cassette and configured to support and cushion a patient's body part during a radiography procedure. The cover comprises a body having a first sheet and a second sheet comprised of a radiolucent, non-plastic material. The first sheet and the second sheet have pairs of opposing ends with one pair of opposing ends being closed and the other pair of opposing end being open to form a sleeve between the first sheet and the second sheet. The cover further comprises a cushion element integrally distributed throughout the first sheet and the second sheet wherein the sleeve is sized and shaped to accept the X-ray cassette and wherein the cushion element cushions the patient during the radiography procedure.

BRIEF DESCRIPTION OF THE SEVERAL VIEWS OF THE DRAWINGS

In the accompanying drawings which form part of the specification:

FIG. 1 illustrates a break away view of a cover constructed in accordance with and embodying the present disclosure and a X-ray cassette being deposited into the cover;

FIG. 2 illustrates another embodiment of the cover of the present disclosure;

FIG. 3 illustrates a side view of the cover of FIG. 1 with the cassette shown positioned within the cover; and FIG. 4 illustrates a side view of a patient's arm resting on the cover during an X-ray procedure.

Corresponding reference numerals indicate corresponding parts throughout the several figures of the drawings.

DESCRIPTION OF THE PREFERRED EMBODIMENT

The following detailed description illustrates the disclosure by way of example and not by way of limitation. The description clearly enables one skilled in the art to make and use the disclosure, describes several embodiments, adaptations, variations, alternatives, and uses of the disclosure, including what is presently believed to be the best mode of carrying out the disclosure.

The present disclosure relates to a cover for a medical device. The cover can be used in any appropriate medical device. However, for purposes of illustration only, the cover will be described as incorporated into a cover for an X-ray cassette.

Referring to the drawings, an X-ray cassette 10 comprises a body 12 which supports and protects a photoreceptive medium such as an X-ray film 14. The body 12 comprises a top 16, a bottom 18 and sides 20 connecting the top 16 and the bottom 18, wherein the top 16, bottom 18 and sides 20 have predetermined wall thicknesses. The top 16, bottom 18 and sides 20 form an enclosure therein for accepting and enclosing the X-ray film 14. The top 16 or one of the sides 20 includes a hinge 22 and an openable flap 24 to allow access to the enclosure. This openable flap 24 is connected to and movable relative to the enclosure to allow the flap to swing open for insertion and extraction of the X-ray film 14.

Generally, cassettes 10 are available in length and height dimensions of 8"×10", 10"×"12", 11"×"14" and 14"×17". Some cassettes 10 incorporate an exterior grid (not shown) which enhances the quality of the resultant image of the X-ray film 14. Thus, the grid increases the overall dimension of the cassette 10. For example, for a 10"×12" cassette having the grid, the external dimensions of the cassette 10 are $10^{15}/_{16}$"× 13¼" and for a 14"×17" cassette having the grid, the external dimensions of the cassette are 15½"×18½".

The body 12, in which the photoreceptive medium sets, can be constructed of lightweight materials such as a thermoplastic material. Further, the body 12 can have a variety of shapes such as elliptical, oval, circular, triangular, square, rectangular or any other appropriate configuration. As shown, the body 12 has a square shape.

A cover 26 of the present disclosure is sized and shaped to enclose the cassette 10 for handling and procedureing the cassette 10 by the health care professional. The cover 26 comprises a first sheet 28, a second sheet 30 and sidewalls 32 connecting the first sheet 28 and the second sheet 30. The sheets 28, 30 and sidewalls 32 have predetermined wall thicknesses. In the embodiment shown, second sheet 30 is slightly longer than the first sheet 28 such that the second sheet 30 extends beyond the first sheet 28 to form flap 34. A fastener (not shown) can be utilized to fasten the flap 34 to the first sheet 28.

In an embodiment (FIG. 2), the first sheet 28 and the second sheet 30 are suitably joined together along edges thereof by a radiolucent seal 36. The seal 36 binds the first sheet 28 and the second sheet 30 in a variety of ways. In one embodiment, heat sealing is used. However, any means of sealing can be used is intended to be within the scope of the present disclosure. In another embodiment, the seal 36 is not radiolucent; however, this seal 36 does not interfere with the radiography. The seal 36 can be formed such that first sheet 28 and second sheet 30 have no discernable seams.

Returning to FIG. 1, cover 26 can have a variety of shapes such as elliptical, oval, circular, triangular, square, rectangular or any other appropriate configuration. As shown, the cover 26 has a rectangular shape. The cover 26 can be sized to enclose any cassette size. Accordingly, the cover 26 of the present disclosure includes dimensions ranging from about six to about sixteen inches for the length and to about eight inches to about twenty inches for the height and to about $1/16$ inch to about six inches for the width. The dimensions are representative of an embodiment and not intended to limit the scope of the disclosure.

Sheets 28, 30 include tops 38, 40, bottoms 42, 44, outer surfaces 46, 48 and inner surfaces 50, 52. The tops 38, 30 are separated from each other to form an opposing and open end of the cover 26. The bottoms 42, 44 are connected to each other to form and opposing and closed end of the cover 26. The inner surfaces 50, 52 form a sleeve 54 therein (FIG. 3). The sleeve 54 allows access space between the first sheet 28 and the second sheet 30 so as to insert the cassette 10 between the first sheet 28 and the second sheet 30. Thus, the cassette 10 fits into and resides between the first sheet 28 and the second sheet 30.

The sheets 28, 30 and sidewalls 33 can be constructed of a variety of impermeable, radiolucent and hospital grade materials. Hospital grade materials include materials namely low in generation of static electricity and substantially free of particulate matter, which could enter an incision. The material of the cover 26 is hospital grade for uses such as but not limited to: Intensive Care Unit and Critical Care Unit where the cassette 10 has to be placed properly; emergency room traumas, where excess fluids may contact the cassette 10; surgery in the sterile field of an operating room or for post-reduction X-ray of fractures where wet, messy plaster can be used. In one embodiment, the cover 26 comprises a fluid resistant, radiolucent material such that the cover 26 does not interfere with the radiograph procedure.

In the illustrated embodiment, the cover 26 is constructed of a non-plastic material. The non-plastic material reduces adhesion of the patient's skin to the cover 26 during patient contact with the cover 26. In one embodiment, the cover 26 comprises a flame-resistant, polyester fabric. The sheets 28, 30 may include anti-microbiological materials dispersed throughout the sheets 28, 30. Further, the sheets 28, 30 may include ecological sensitive materials such as post-consumer, recycled polyester or low chemical emission materials.

In the embodiment shown, the sheets 28, 30 include an integrated cushion element 56 dispersed throughout the sheets 28, 30. As shown, sidewalls 32 also include cushion elements 56. The cushion element 56 is comprised of radiolucent material. In one embodiment, cushion element 56 comprises a plurality of cushion elements 56. Any number of cushioned elements 56 easily used for the intended purpose is acceptable. The cushioned element 56 provides uniform padding for the entire cover 26. The cushion element 56 is sized and shaped to accept and to cushion the patient's body part during the X-ray procedure (FIG. 4).

Since the sheets 28, 30 include the uniformly dispersed cushion elements 56, the hospital personnel can conveniently use any sheet 28, 30 of the cover 26 to support the patient's body part while placing the other sheet 28, 30 of the cover 26 on the appropriate support such as a gurney or operating table (FIG. 4). The uniformly dispersed cushion element 56 maintains a symmetric configuration for the cover 26 to eliminate one side of the cover 26 being more bulky or thicker than the other side of the cover. The symmetric configuration of the cover 26 assists in storage, handling and disposal of the cover 26.

In an embodiment (not shown), the cushion element 56 includes absorbent material to absorb fluid or blood of the patient. In this embodiment, the cushion element 56 absorbs the patient's fluid to assist in hygienic disposal of the cover 26 when the cover 26 becomes contaminated.

During use, the health care professional conveniently grasps the cover 26 (which may be positioned within protective packaging) from storage and carries the cover 26 to a sterile field such as an operating room or sterile table. At the sterile field, the user removes the cover 26 from any protective packaging and opens the first sheet 28 and the second sheet 30 to expose the sleeve 54. Next the user inserts the X-ray cassette 10 into the sleeve 54 and between the first sheet 28 and the second sheet 30. The health care professional folds the flap 34 over the sleeve 54 and in contact with the first sheet 28.

The user then fastens the flap 34 to the first sheet 28 and places the cover 26 on the suitable surface. The patient's body part is placed on the cover 26 to begin the X-ray procedure wherein the cover 26 and the enclosed X-ray cassette 10 support the patient's body part. The non-plastic material of the cover 26 prevents adhesion of the patient's skin to the cover 26. Additionally, the cushion element 56 provides cushioning for the patient's body part during the X-ray procedure. Further, the material of the cover 26 or the cushion element 56 absorbs patient fluid from the patient's body part. After removal of the cassette 10 from the sleeve 54, the health care professional easily disposes of the cover 26 and absorbed fluid into the appropriate bio-hazard disposal or waste disposal.

As various changes could be made in the above constructions without departing from the scope of the disclosure, it is intended that all matter contained in the above description or shown in the accompanying drawings shall be interpreted as illustrative and not in a limiting sense. Moreover, the use of the terms "inner" and "outer" or "top" or "bottom" or "first or "second"" and variations of these terms is made for convenience, but does not require any particular orientation of the components.

The invention claimed is:

1. A sterile cover configured to seal an X-ray cassette and configured to support and cushion a patient's body part during an X-ray procedure, the cover comprising: a body having a first sheet and a second sheet, the first sheet and the second sheet being comprised of a radiolucent, non-plastic material, the body further having a sidewall connecting together the first sheet and the second sheet, the first sheet and the second sheet having pairs of opposing ends with one pair of opposing ends being closed and the other pair of opposing end being open to form a sleeve between the first sheet and the second sheet; and a cushion element integrally distributed throughout the first sheet and the second sheet, said sleeve sized and shaped to accept the X-ray cassette, said cushion element sized and shaped to cushion the patient's body part during the X-ray procedure wherein the cushion element comprises a fluid absorbent material.

2. The sterile cover of claim 1 wherein the cushion element comprises a plurality of cushion elements.

3. The sterile cover of claim 1 wherein the plurality of cushion elements are uniformly distributed throughout the first sheet and the second sheet.

4. The sterile cover of claim 1 wherein the first sheet and the second sheet have lengths from about six inches to about sixteen inches and a height from about eight inches to about 20 inches.

* * * * *